(12) United States Patent
Koermer et al.

(10) Patent No.: US 6,440,900 B1
(45) Date of Patent: Aug. 27, 2002

(54) METHOD FOR EXTENDING THE LIFE OF CUT FLOWERS

(75) Inventors: Gerald S. Koermer, Roseland, NJ (US); Timothy D. Wldman, Metamora, IN (US)

(73) Assignee: Engelhard Corporation, Iselin, NJ (US)

( * ) Notice: Subject to any disclaimer, the term of this patent is extended or adjusted under 35 U.S.C. 154(b) by 0 days.

(21) Appl. No.: 09/860,194

(22) Filed: May 15, 2001

(51) Int. Cl.[7] ................................................. A01N 3/02
(52) U.S. Cl. ...................................................... 504/114
(58) Field of Search ......................................... 504/114

(56) References Cited

U.S. PATENT DOCUMENTS

| | | | |
|---|---|---|---|
| 5,080,707 A | 1/1992 | Ide ............................... 71/68 |
| 5,284,818 A | 2/1994 | Shafer et al. ................ 504/115 |
| 5,366,954 A | 11/1994 | Bestwick et al. ............ 504/114 |
| 5,421,121 A | 6/1995 | Bestwick et al. ........... 47/41.01 |
| 5,536,155 A | 7/1996 | Futaki et al. ................ 424/195 |
| 5,580,975 A | 12/1996 | Tada ........................... 536/123 |
| 5,635,443 A | 6/1997 | Lesenko ...................... 504/114 |
| 5,965,264 A | 10/1999 | Barenberg et al. ........... 428/402 |
| 6,277,408 B1 * | 8/2001 | Wellinghoff et al. ......... 424/473 |

FOREIGN PATENT DOCUMENTS

JP 4-166072 * 4/1992

* cited by examiner

*Primary Examiner*—S. Mark Clardy
(74) *Attorney, Agent, or Firm*—Stephen I. Miller

(57) ABSTRACT

Method for extending the life of cut flowers such as roses by bathing the stems of the flowers in a storage solution which contains chlorine dioxide. Also disclosed are compositions for use in the method.

25 Claims, No Drawings

METHOD FOR EXTENDING THE LIFE OF CUT FLOWERS

FIELD OF THE INVENTION

The present invention relates to a method for extending the life of cut flowers such as roses. In particular, the present invention relates to the use of an aqueous solution of chlorine dioxide for extending the life of such cut flowers.

BACKGROUND OF THE INVENTION

It is known that the useful lifetime of cut flowers can be extended by refrigeration and by use of certain chemical preservatives. The fact that many flower varieties are shipped as cut flowers over long distances has provided a need for improved methods of extending the life of cut flowers. Placing cut flowers in water affords some measure of preservation by keeping the flowers hydrated, but chemical preservatives are often added to water solutions to further extend the life of the cut flower.

Among the chemical preservatives currently in use are carbohydrates such as sucrose, fructose and glucose, acidifing agents for producing a solution pH of 3 to 7, agents for preventing stem blockage, etc. Several preservative compositions which contain various mixtures of the foregoing are commercially available, e.g., Chrysal™, Floralife™, and the like.

Frequently, bleach is used as a biocide by florists to sterilize storage containers which are to hold the cut flowers as well as for sterilization of pumping apparatus and tubing used to deliver storage solution to the storage containers. Although bleach is quite cheap, it produces an undesirable basic pH in the solution and florists do not like handling bleach solutions. Moreover, the bleach remains in the storage solution for a prolonged period of time and is toxic to many flowers which are stored in such bleach solutions for prolonged periods of time.

SUMMARY OF THE INVENTION

It is the object of the present invention to provide a method for extending the life of cut flowers, especially roses.

The method of the present invention comprises: (a) providing a storage solution containing chlorine dioxide; and (b) bathing the stem of the cut flower in the solution.

DETAILED DESCRIPTION OF THE INVENTION

As mentioned above, the method of the present invention comprises: (a) providing a storage solution containing chlorine dioxide; and (b) bathing the stem of the cut flower in the solution. In general, the concentration of the chlorine dioxide in the solution is in the range of about 1 to about 25 parts per million, based on the weight of the solution. Preferably, the concentration of the chlorine dioxide in the solution is in the range of 4 to 10 parts per million, based on the weight of the solution. In order to insure the maximum beneficial effect of the solution, it is preferred that the stems of the cut flowers be immersed in the solution immediately after harvesting the flowers.

Especially good results have been achieved wherein the cut flower is a rose. Preferably, the rose is again cut again, while submerged either in water which is subsequently converted into the solution or in the solution itself, in order to avoid the formation of air bubbles in the stem which would impede the transport of the solution through the stem.

The storage solution is prepared by adding a combination of an alkali metal or alkaline earth metal chlorite, e.g., sodium chlorite, and a solid acid, e.g., sodium bisulfate, to water. Preferably, the molar ratio of chlorite to acid in the combination is in the range of about 0.5:1 to about 1.5:1. In general, the combination is present in the form of a massive body, e.g., in the form of agglomerates or tablets. Tablets represent a convenient form for preparation of the solution. In general, a tablet having a weight of about 0.1 to about 10 grams, preferably a weight of 1 to 5 grams has been found to be most useful for preparing the solution. The solution is readily prepared by adding 1–3 tablets to about one gallon of water.

Preferably, the tablet contains one or more desiccants present in an amount of about 5 to about 20 wt. %, based on the weight of the tablet. Suitable desiccants include calcium chloride, magnesium chloride and magnesium sulfate. It is also preferred that the tablet includes one or more promoters, present in an amount of about 1 to about 10 wt. %, based on the weight of the tablet. Suitable promoters include sodium chloride, potassium chloride and an isocyanurate.

It is also preferred that the tablet contains one or more sugars, present in an amount of about 0.5 to about 10 grams per gallon of solution. Suitable sugars include ribose, arabinose, xylose, lyxose, allose, altrose, glucose, mannose, gulose, idose, galactose, talose, fructose, alkyl-α-glycosides, aryl-α-glycosides, alkyl-β-glycosides, aryl-β-glycosides, lactose, maltose, cellobiose, gentiobiose, turanose, iso-maltose, laminaribose, melibiose, sucrose, trehalose, raffinose and gentianose.

In order to accelerate the dissolution the tablet in the water to form the solution, it is preferred that the tablet contain an effervescing agent, e.g., sodium bicarbonate, in an amount of about 2 to about 12 wt. % based on the weight of the tablet.

The following nonlimiting examples are presented to illustrate the invention. Unless otherwise indicated, all amounts and percentages are on a weight basis.

EXAMPLE 1

In the following examples, test were conducted with fresh red roses obtained from a single source. The stems were cut (under water) and, for each experimental test, 5 roses were placed in a beaker. The same person monitored the flowers every day (the criterion for bloom death was that the monitor would have discarded the roses if the roses were in the monitor's home). Thereafter, the average flower life in days was calculated for each experimental condition.

Five beakers of 800 ml tap water containing 0, 2, 5, 10 and 15 ppm chlorine dioxide were used for these tests. The results of these tests are set forth in Table 1:

TABLE 1

| Chlorine Dioxide Level, ppm | Average Flower Life, days |
| --- | --- |
| 0 | 4.0 |
| 2 | 5.6 |
| 5 | 7.8 |
| 10 | 5.8 |
| 15 | 5.8 |

As may be seen from the results set forth in Table 1, the roses in the beaker containing no chlorine dioxide had the shortest lifetime. The dosage of 5 ppm chlorine dioxide appear to be optimal and, at such concentration, the lifetime of the roses was approximately doubled. Roses with less or more chlorine dioxide had intermediate lifetimes. Spectroscopic evaluation of the flower water on the third day of the tests indicated that no chlorine dioxide was present. This was not surprising since the beakers were uncovered and chlorine dioxide could readily escape or decompose.

EXAMPLE 2

Example 1 was repeated using tap water alone, tap water containing 5 ppm chlorine dioxide, tap water containing "Aquaplus®" and tap water containing 5 ppm chlorine dioxide and "Aquaplus®". "Aquaplus®" is described as a fresh flower nutrient and water clarifier and was obtained from Syndicate Sales, Kokomo, Ind. The results of these tests are set forth in Table 2:

TABLE 2

| Flower Treatment | Flower Lifetime, days |
| --- | --- |
| Plain Water | 4.0 |
| 5 ppm $ClO_2$ | 7.8 |
| "Aquaplus ®" (no $ClO_2$) | 6.2 |
| 5 ppm $ClO_2$ and "Aquaplus ®" | 11.6 |

As may be seen from the results set forth in Table 2, the roses in the beaker containing no chlorine dioxide had the shortest lifetime. The use of "Aquaplus®" alone increased the lifetime by about 50%. The use of chlorine dioxide in a concentration of 5 ppm approximately doubled the lifetime, while the use of chlorine dioxide in a concentration of 5 ppm and "Aquaplus®" approximately tripled the lifetime as compared to the plain water control. Further, the use of chlorine dioxide in a concentration of 5 ppm and "Aquaplus®" nearly doubled the lifetime as compared to "Aquaplus®" alone.

The results of these examples clearly indicate that the use of chlorine dioxide produces a beneficial effect on fresh flower lifetime. Furthermore, it appears that chlorine dioxide plus a flower food affords results that are nearly additive, thus suggesting that the mechanisms for each treatment are probably independent of one another. These results also indicate that flower food does not react quickly with chlorine dioxide. Accordingly, it appears that solutions containing chlorine dioxide would enable a florist to sanitize, clean and maintain mechanical flower food dosing systems without the need to employ time consuming procedures to thoroughly flush the system to remove agents such as bleach.

What is claimed is:

1. A method for extending the life of a cut flower comprising:
   (a) providing an aqueous storage solution containing chlorine dioxide; and
   (b) bathing the stem of the cut flower in the solution.

2. The method of claim 1 wherein the concentration of the chlotine dioxide in the solution is in the range of about 1 to about 15 parts per million, based on the weight of the solution.

3. The method of claim 2 wherein the concentration of the chlorine dioxide in the solution is in the range of 4 to 10 parts per million, based on the weight of the solution.

4. The method of claim 1 wherein said bathing is initiated immediately after harvesting the cut flower.

5. The method of claim 1 wherein the cut flower is a rose.

6. The method of claim 5 wherein the stem of the rose is re-cut while being immersed in: (a) water which is thereafter converted to said solution or (b) said solution.

7. The method of claim 1 wherein the solution is prepared by adding a combination of an alkali metal or alkaline earth metal chlorite and a solid acid to water.

8. The method of claim 7 wherein the molar ratio of chlorite to acid in the combination is in the range of about 0.5:1 to about 1.5:1.

9. The method of claim 7 wherein the combination is present in the form of a massive body.

10. The method of claim 7 wherein the massive body is present in the form of agglomerates or tablets.

11. The method of claim 10 wherein the combination is present in the form of a tablet having a weight of about 0.1 to about 10 grams.

12. The method of claim 11 wherein the tablet has a weight of 1 to 5 grams.

13. The method of claim 12 wherein the solution is prepared by adding 1–3 tablets to about one gallon of water.

14. The method of claim 7 wherein the chlorite comprises sodium chlorite.

15. The method of claim 7 wherein the solid acid comprises sodium bisulfate.

16. The method of claim 11 wherein the tablet contains one or more desiccants selected from the group consisting of calcium chloride, magnesium chloride and magnesium sulfate.

17. The method of claim 16 wherein the desiccant is present in an amount of about 5 to about 20 wt. %, based on the weight of the tablet.

18. The method of claim 11 wherein the tablet includes one or more promoters selected from the group consisting of sodium chloride, potassium chloride and an isocyanurate.

19. The method of claim 18 wherein the promoter is present in an amount of about 1 to about 10 wt. %, based on the weight of the tablet.

20. The method of claim 1 wherein the solution further comprises a sugar.

21. The method of claim 20 wherein the sugar is selected from the group consisting of ribose, arabinose, xylose, lyxose, allose, altrose, glucose, mannose, gulose, idose, galactose, talose, fructose, alkyl-α-glycosides, aryl-α-glycosides, alkyl-β-glycosides, aryl-β-glycosides, lactose, maltose, cellobiose, gentiobiose, turanose, iso-maltose, laminaribose, melibiose, sucrose, trehalose, raffinose and gentianose.

22. The method of claim 20 wherein the sugar is present in an amount of about 0.5 to about 10 grams per gallon of solution.

23. The method of claim 11 wherein the tablet contains an effervescing agent.

24. The method of claim 23 wherein the effervescing agent comprises sodium bicarbonate.

25. The method of claim 23 wherein the effervescing agent is present in an amount of about 2 to about 12 wt. % based on the weight of the tablet.

* * * * *